US00PP13355P2

(12) United States Plant Patent
Rosborg

(10) Patent No.: US PP13,355 P2
(45) Date of Patent: Dec. 17, 2002

(54) KALANCHOE PLANT NAMED 'SAMBA'

(75) Inventor: Lars Rosborg, Odense (DK)

(73) Assignee: Gartneriet Rosborg Bellinge A/S, Odense (DK)

( * ) Notice: Subject to any disclaimer, the term of this patent is extended or adjusted under 35 U.S.C. 154(b) by 0 days.

(21) Appl. No.: 10/103,943

(22) Filed: Mar. 22, 2002

(51) Int. Cl.[7] ..... A01H 5/00
(52) U.S. Cl. ..... Plt./341
(58) Field of Search ..... Plt./338, 339, 341

(56) References Cited

PUBLICATIONS

UPOV ROM GTITM Computer Database, GTI JOUVE Retrieval Software 2002/02, Citation(S) for 'Samba'.*

* cited by examiner

*Primary Examiner*—Bruce R. Campell
*Assistant Examiner*—W C Baker
(74) *Attorney, Agent, or Firm*—C. A. Whealy

(57) ABSTRACT

A new and distinct cultivar of Kalanchoe plant named 'Samba', characterized by its compact and upright plant habit; freely flowering habit; orange red-colored flowers; dark green leaves; good postproduction longevity; and resistance to Powdery Mildew.

1 Drawing Sheet

BOTANICAL CLASSIFICATION/CULTIVAR DESIGNATION

*Kalanchoe blossfeldiana* cultivar Samba.

BACKGROUND OF THE INVENTION

The present invention relates to a new and distinct cultivar of Kalanchoe plant, botanically known as *Kalanchoe blossfeldiana*, and hereinafter referred to by the name 'Samba'.

The new Kalanchoe is a product of the planned breeding program conducted by the Inventor in Odense, Denmark. The objective of the breeding program was to create new early-flowering Kalanchoe cultivars with bright and attractive flower colors and good postproduction longevity.

The new Kalanchoe originated from a cross-pollination made by the Inventor in Odense, Denmark of two unidentified proprietary selections of Kalanchoe, not patented. The new Kalanchoe was discovered and selected by the Inventor within the progeny of the stated cross in a controlled environment in Odense, Denmark. The selection of this plant was based on its flower color.

Asexual reproduction of the new Kalanchoe by terminal cuttings taken at Odense, Denmark, by the Inventor, has shown that the unique features of this new Kalanchoe are stable and reproduced true to type in successive generations.

BRIEF SUMMARY OF THE INVENTION

The cultivar Samba has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Samba'. These characteristics in combination distinguish 'Samba' as a new and distinct cultivar:

1. Compact and upright plant habit.
2. Freely flowering habit.
3. Orange red-colored flowers.

4. Dark green leaves.
5. Good postproduction longevity.
6. Resistant to Powdery Mildew.

Plants of the new Kalanchoe differ primarily from plants of the parent selections in flower color.

Plants of the new Kalanchoe can be compared to plants of the cultivar Apricot Revolution, not patented. In side-by-side comparisons conducted in Odense, Denmark, plants of the new Kalanchoe differed from plants of the cultivar Apricot Revolution in the following characteristics:

1. Flower color of plants of the new Kalanchoe was darker than flower color of plants of the cultivar Apricot Revolution.
2. Plants of the new Kalanchoe had better postproduction longevity than plants of the cultivar Apricot Revolution.
3. Plants of the new Kalanchoe were more resistant to Powdery Mildew than plants of the cultivar Apricot Revolution.

BRIEF DESCRIPTION OF THE PHOTOGRAPHS

The accompanying colored photographs illustrate the overall appearance of the new Kalanchoe, showing the colors as true as it is reasonably possible to obtain in colored reproductions of this type. Colors in the photographs differ slightly from the color values cited in the detailed botanical description which accurately describe the colors of the new Kalanchoe.

The photograph at the top of the sheet comprises a side perspective view of a typical potted plant of 'Samba'.

The photograph at the bottom of the sheet is a close-up view of the following: side and top perspective views of typical flowering cymes, side perspective view of a single flower, and top perspective views of young and fully expanded leaves of 'Samba'.

DETAILED BOTANICAL DESCRIPTION

In the following description, color references are made to The Royal Horticultural Society Colour Chart, 1995 Edition, except where general terms of ordinary dictionary significance are used. Plants used in the aforementioned photographs and for the following observations and measurements were grown in Odense, Denmark, during the autumn under commercial practice in a glass-covered greenhouse for about 14 to 18 weeks in 10.5-cm containers. Plants were exposed to photoinductive short day/long night conditions for the last 10 weeks of production. During the production of the plants, day and night temperatures averaged 20 and 18° C., respectively, Plants used in the photographs and description were not pinched.

Botanical classification: *Kalanchoe blossfeldiana* cultivar Samba.

Parentage:

*Female, or seed, parent*.—Unidentified proprietary selection of *Kalanchoe blossfeldiana*, not patented.

*Male, or pollen, parent*.—Unidentified proprietary selection of *Kalanchoe blossfeldiana*, not patented.

Propagation:

*Type cutting*.—Terminal cuttings.

*Time to initiate roots, summer and winter*.—About 10 days at 20° C.

*Root description*.—Fibrous, well-branched.

Plant description:

*Form*.—Compact and upright plant habit with rounded crown. Plants are appropriate for 10.5-cm containers.

*Branching habit*.—Freely branching, about four lateral branches develop. Pinching (removal of terminal apex) is not required but will enhance lateral branch development.

*Plant height at flowering*.—About 25 cm.

*Plant diameter at flowering*.—About 23 cm.

*Lateral branch length*.—About 18 cm.

*Lateral branch diameter*.—About 4 mm.

*Internode length*.—About 1.5 cm.

*Stem texture*.—Smooth, glabrous.

*Stem color*.—138A.

Foliage description: Unless otherwise specified, the foliage description represents leaves from a vegetative plant.

*Arrangement*.—Simple, opposite.

*Size, vegetative plants*.—Length: About 12.9 cm. Width: About 8.6 cm.

*Size, reproductive plants*.—Length: About 8.5 cm. Width: About 6.8 cm.

*Shape*.—Rounded oval.

*Apex*.—Obtuse.

*Base*.—Obtuse.

*Margin*.—Crenate; undulate.

*Aspect*.—Initially slightly concave, then convex.

*Texture, upper and lower surfaces*.—Leathery, glabrous, succulent, rugose.

*Venation pattern*.—Pinnate.

*Color*.—Young foliage, upper surface: 137A. Young foliage, lower surface: 137C. Fully expanded foliage, upper surface: 133A. Fully expanded foliage, lower surface: 137B. Venation, upper and lower surfaces: Same as lamina color.

*Petiole*.—Length: About 2.1 cm. Diameter: About 1 cm. Texture: Smooth, glabrous. Color, upper surface: 137D. Color, lower surface: 138D.

Flower description:

*Flower type and habit*.—Single flowers arranged in compound dichasial cymes that arise from leaf axils; flowers face mostly upright. Freely flowering, about 275 flowers will develop per plant. Flowers persistant. Flowers not fragrant.

*Natural flowering season*.—Late autumn/winter/early spring. Flower initiation and development can be induced under photoinductive short day/long night conditions.

*Time to flower*.—About 11 weeks of photoinductive short day/long night conditions are required to produce flowering plants.

*Flower opening*.—First flower open is the terminal flower at the main axis and is followed by the opening of the terminal flowers of the side branches of the inflorescence.

*Post-production longevity*.—Flowers of plants of the new Kalanchoe maintain good substance for about nine weeks under greenhouse conditions.

*Flower diameter*.—About 1.8 cm.

*Flower depth* (*height*).—About 1.6 cm.

*Flower buds*.—Shape: Oblong. Length: About 1.2 cm. Width: About 3 mm. Color: 39C.

*Petals*.—Quantity: Four fused at base. Length: About 8 mm. Diameter: About 8.5 mm. Shape: Rounded oval. Apex: Cuspidate. Margin: Entire. Texture, upper and lower surfaces: Smooth, glabrous. Color: When opening, upper surface: 34A. When opening, lower surface: 39B. Fully opened, upper surface: 43A; color does not fade with subsequent development. Fully opened, lower surface: 39B.

*Sepals*.—Quantity: Four fused at base. Length: About 9 mm. Diameter: About 3 mm. Shape: Ovate. Apex: Acute. Margin: Entire. Texture, upper and lower surfaces: Smooth, glabrous. Color, immature, upper and lower surfaces: 144A. Color, mature, upper and lower surfaces: 138A.

*Reproductive organs*.—Stamens: Stamen number: Eight per flower. Anther shape: Oval. Anther length: About 1 mm. Anther color: 22A. Pollen color: Close to 3C. Pistils: Pistil number: Four per flower. Pistil length: About 8 mm. Style length: About 2.5 mm. Style color: 154C. Stigma shape: Round. Stigma color: 157D. Ovaries: Superior and four-celled. Ovary color: 144B.

*Seed/fruit*.—Seed and fruit production has not been observed.

Disease/pest resistance: Plants of the new Kalanchoe have been observed to be resistant to Powdery Mildew. Resistance to known Kalanchoe pests has not been observed on plants of the new Kalanchoe grown under commercial greenhouse conditions.

It is claimed:

1. A new and distinct cultivar of Kalanchoe plant named 'Samba', as illustrated and described.

* * * * *

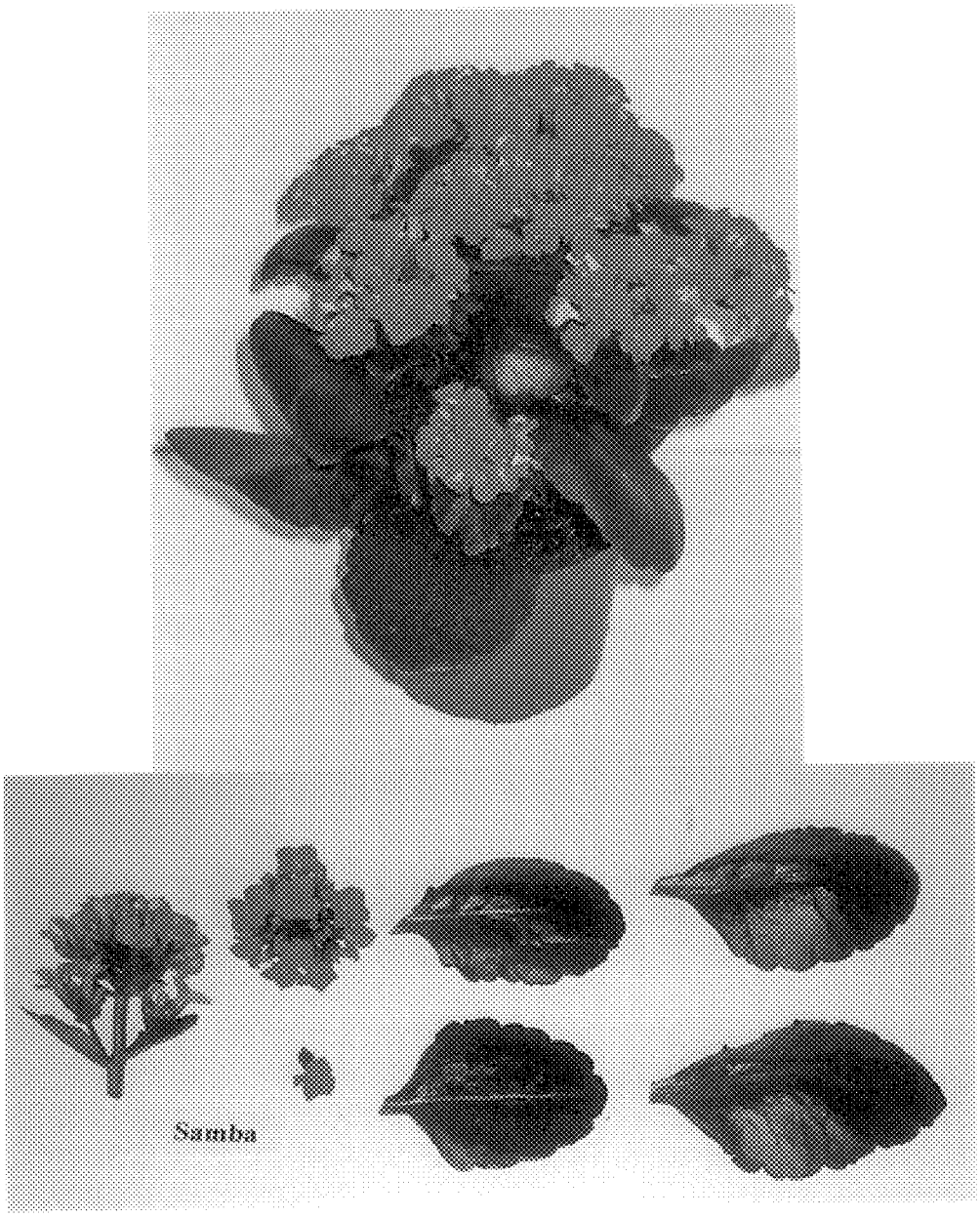
Samba